United States Patent
Biedermann

(10) Patent No.: US 11,213,323 B2
(45) Date of Patent: Jan. 4, 2022

(54) COUPLING DEVICE AND INSTRUMENT FOR CONNECTING THE COUPLING DEVICE TO A HEAD OF A BONE ANCHOR

(71) Applicant: BIEDERMANN TECHNOLOGIES GMBH & CO. KG, Donaueschingen (DE)

(72) Inventor: Timo Biedermann, Trossingen (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 0 days.

(21) Appl. No.: 17/123,959

(22) Filed: Dec. 16, 2020

(65) Prior Publication Data
US 2021/0186569 A1 Jun. 24, 2021

Related U.S. Application Data

(60) Provisional application No. 62/949,872, filed on Dec. 18, 2019.

(30) Foreign Application Priority Data

Dec. 18, 2019 (EP) .................................. 19217559

(51) Int. Cl.
A61B 17/70 (2006.01)
A61B 17/86 (2006.01)

(52) U.S. Cl.
CPC ...... *A61B 17/7034* (2013.01); *A61B 17/7046* (2013.01); *A61B 17/7082* (2013.01); *A61B 17/8695* (2013.01)

(58) Field of Classification Search
CPC ...... A61B 17/70; A61B 17/7034–7046; A61B 17/7074; A61B 17/7076–708; A61B 17/7082
See application file for complete search history.

(56) References Cited

U.S. PATENT DOCUMENTS

| 5,672,176 A | 9/1997 | Biedermann et al. |
| 6,440,133 B1 | 8/2002 | Beale et al. |
| (Continued) | | |

FOREIGN PATENT DOCUMENTS

| CN | 102149344 A | 8/2011 |
| EP | 1 105 057 | 2/2001 |
| (Continued) | | |

OTHER PUBLICATIONS

Extended European Search Report for Application No. 19217559.4, dated Sep. 4, 2020, 14 pages.

(Continued)

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A coupling device includes a receiving part having a head receiving portion for pivotably receiving a head of a bone anchor and a rod receiving portion defining a recess for receiving the rod, the rod receiving portion having an engagement structure for engaging a locking member to lock the rod in the recess and a first engagement surface different from the engagement structure for engaging an instrument, wherein the first engagement surface is formed away from radially outwardly facing regions of the rod receiving portion, and a locking ring positionable around the head receiving portion and having a second engagement surface for engaging the instrument. The locking ring can assume an insertion position where the head of the bone anchor is insertable into the head receiving portion, and a pre-locking position where the head is prevented from removal from the head receiving portion.

22 Claims, 12 Drawing Sheets

(56) References Cited

U.S. PATENT DOCUMENTS

| | | |
|---|---|---|
| 6,471,705 B1 | 10/2002 | Biedermann et al. |
| 8,192,470 B2 | 6/2012 | Biedermann et al. |
| 8,328,817 B2 | 12/2012 | Strauss |
| 8,852,239 B2 | 10/2014 | Jackson et al. |
| 9,308,027 B2 | 4/2016 | Jackson |
| 9,480,517 B2 | 11/2016 | Jackson et al. |
| 9,895,171 B2 | 2/2018 | Webb |
| 10,258,390 B2 | 4/2019 | Biedermann et al. |
| 2003/0023243 A1 | 1/2003 | Biedermann et al. |
| 2003/0125741 A1 | 7/2003 | Biedermann et al. |
| 2004/0225289 A1 | 11/2004 | Biedermann et al. |
| 2007/0043378 A1 | 2/2007 | Kumar et al. |
| 2007/0161998 A1 | 7/2007 | Whipple |
| 2007/0162009 A1 | 7/2007 | Chao et al. |
| 2008/0200918 A1 | 8/2008 | Spitler et al. |
| 2009/0105712 A1 | 4/2009 | Dauster et al. |
| 2009/0163963 A1 | 6/2009 | Berrevoets |
| 2009/0264896 A1 | 10/2009 | Biedermann et al. |
| 2010/0114108 A1 | 5/2010 | Strauss |
| 2011/0046683 A1 | 2/2011 | Biedermann et al. |
| 2011/0152949 A1 | 6/2011 | Biedermann et al. |
| 2011/0166606 A1 | 7/2011 | Stihl et al. |
| 2011/0263945 A1 | 10/2011 | Peterson et al. |
| 2011/0282402 A1 | 11/2011 | Chao et al. |
| 2012/0068413 A1 | 3/2012 | Putt et al. |
| 2012/0239092 A1 | 9/2012 | Jones et al. |
| 2012/0253402 A1 | 10/2012 | McLean |
| 2012/0296171 A1 | 11/2012 | Lovell et al. |
| 2013/0018428 A1 | 1/2013 | Harper et al. |
| 2013/0023941 A1 | 1/2013 | Jackson et al. |
| 2013/0060293 A1 | 3/2013 | Jackson et al. |
| 2013/0085536 A1* | 4/2013 | Biedermann ...... A61B 17/7035 606/308 |
| 2013/0144346 A1 | 6/2013 | Jackson et al. |
| 2014/0188175 A1 | 7/2014 | Mishra et al. |
| 2015/0250512 A1* | 9/2015 | Poker ............. A61B 17/7037 606/305 |
| 2016/0066957 A1* | 3/2016 | Biedermann ...... A61B 17/7076 606/272 |
| 2017/0020574 A1* | 1/2017 | Biedermann ...... A61B 17/7076 |
| 2018/0055542 A1 | 3/2018 | Biedermann |
| 2018/0055545 A1 | 3/2018 | Biedermann et al. |
| 2019/0192192 A1 | 6/2019 | Biedermann et al. |

FOREIGN PATENT DOCUMENTS

| | | |
|---|---|---|
| EP | 2 918 236 A1 | 9/2015 |
| EP | 3 106 110 A1 | 12/2016 |
| JP | 2013-540453 A | 11/2013 |
| WO | WO 2011/159492 A1 | 12/2011 |
| WO | WO 2013/187928 A1 | 12/2013 |

OTHER PUBLICATIONS

Extended European Search Report for Application No. 14160126.0, dated Jan. 5, 2015 (12 pages).

European Search Report; Application Serial No. 14160126.0; dated Aug. 1, 2014; Completion Date Jul. 25, 2014; 5 Sheets.

* cited by examiner

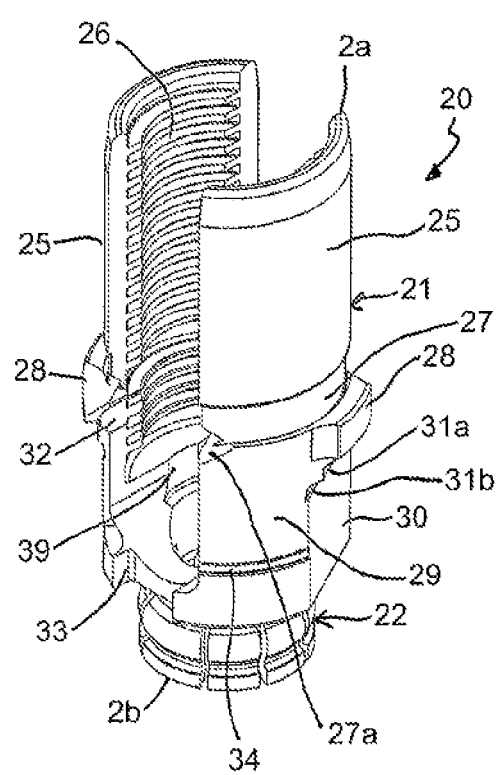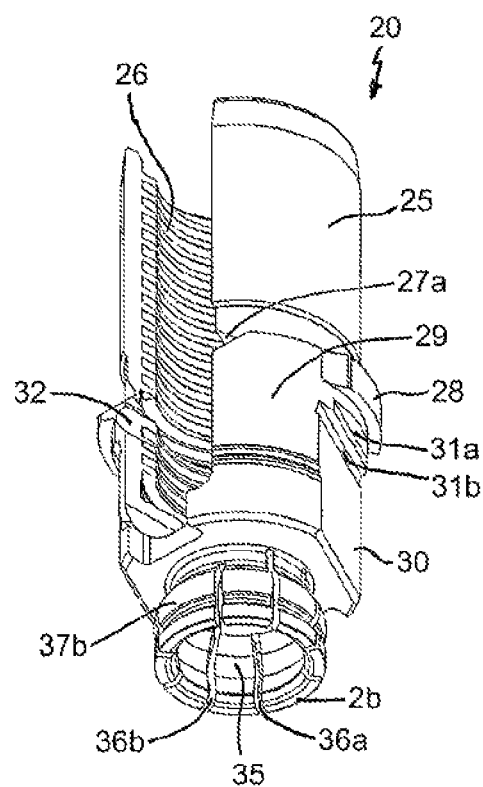
Fig. 4    Fig. 5
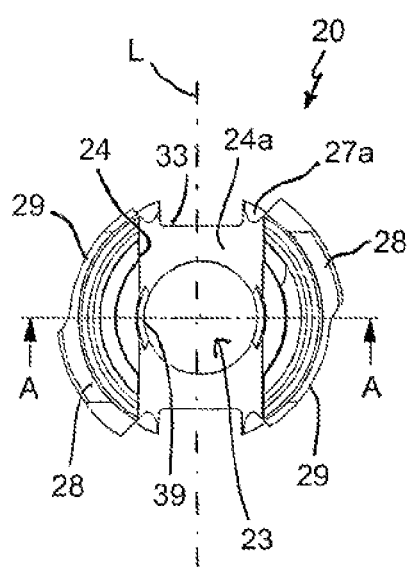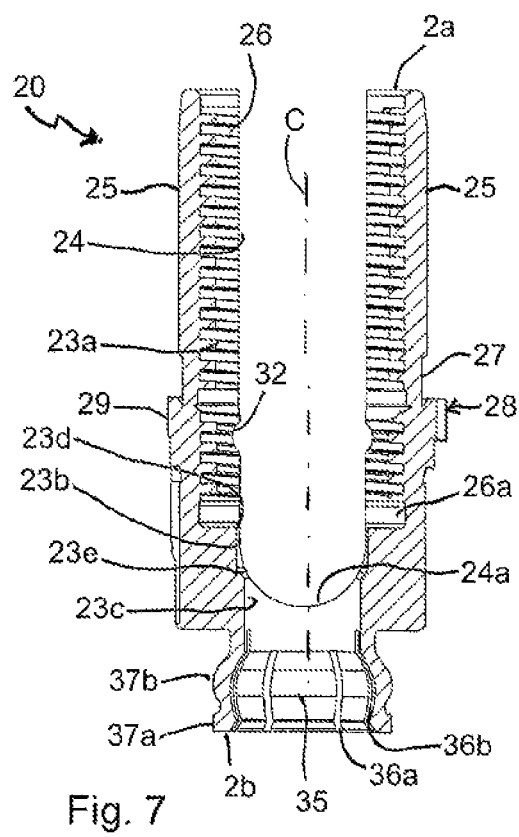
Fig. 6    Fig. 7

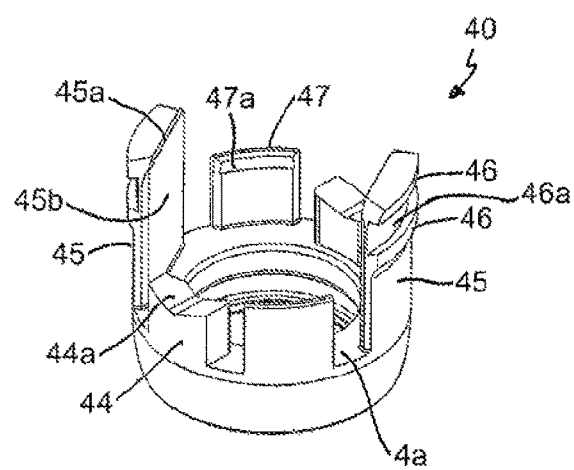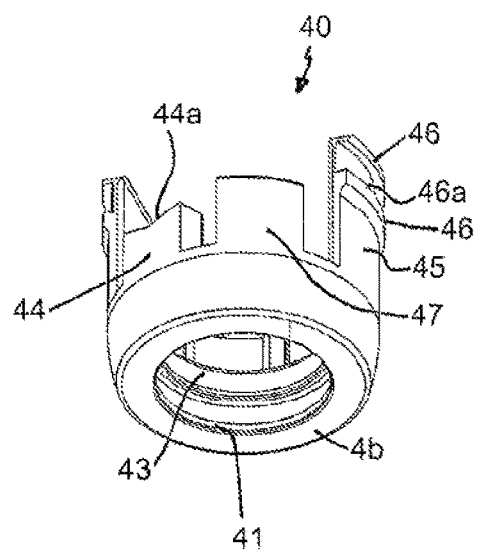
Fig. 8    Fig. 9
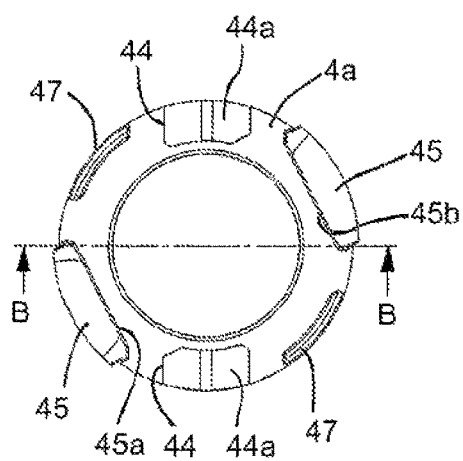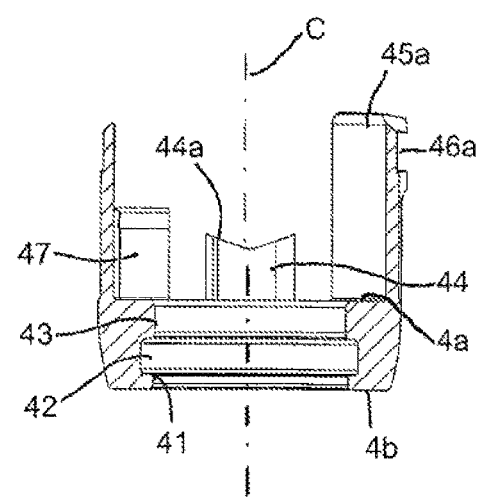
Fig. 10    Fig. 11

COUPLING DEVICE AND INSTRUMENT FOR CONNECTING THE COUPLING DEVICE TO A HEAD OF A BONE ANCHOR

CROSS-REFERENCE TO RELATED APPLICATION(S)

The present application claims priority to and the benefit of U.S. Provisional Patent Application No. 62/949,872, filed Dec. 18, 2019, the contents of which are hereby incorporated by reference in their entirety, and claims priority from European Patent Application EP 19 217 559.4, filed Dec. 18, 2019, the contents of which are hereby incorporated by reference in their entirety.

BACKGROUND

Field

The application relates to a coupling device for coupling a rod to a bone anchor and to an instrument for connecting the coupling device to a head of the bone anchor. More specifically, the invention relates to a coupling device and to an instrument which permits placement of a receiving part with an outer locking ring onto the head in situ, i.e., in a condition in which the bone anchor has already been inserted into a bone or a vertebra with the head protruding out of the bone surface.

Description of Related Art

A coupling device with an outer locking ring that is arranged around a head receiving portion is known, for example, from US 2018/0055545 A1. The coupling device is part of a polyaxial bone anchoring device that includes a receiving part with a rod receiving portion and a head receiving portion and a locking ring arranged around the head receiving portion which forms a compression member to exert pressure onto an inserted head. The head receiving portion has a plurality of slits that render the head receiving portion flexible so that when pressure is exerted onto the head receiving portion by the locking ring, the head can be clamped and finally locked. An instrument for moving the locking ring from an insertion position for the head to a locking position for the head and vice versa is also described in the document. Usually, the bone anchoring device is pre-assembled with the bone anchor.

U.S. Pat. No. 10,258,390 B2 describes a device for placing a receiving part of a bone anchoring device onto a head of a bone anchoring element, which includes a holding portion, a collet configured to be held in the holding portion, the collet having a tubular body and a distal end portion configured to be flexibly expanded and compressed in a radial direction, and a plunger configured to be positioned in the collet. With the device it is possible to engage the receiving part at an inner wall and to place it onto the bone anchor that has been already inserted into a bone. The bone anchoring device described in the document is of the type using an inner cap placed in the receiving part as a compression member for exerting pressure onto the head with a rod or a locking member to lock the head.

SUMMARY

While bone anchoring devices using an inner cap for clamping and locking the head described in the prior art may be appropriate for a number of clinical applications, there is still a need for an alternative and/or improved bone anchoring device which allows in situ placement of a coupling device including a receiving part and a compression member onto an implanted bone anchor.

It is therefore an object of the present invention to provide a coupling device and an instrument for use with such a coupling device that is improved compared to known devices.

A coupling device according to embodiments of the invention may include an outer locking ring as a compression member to exert pressure onto the head, and can be placed onto a bone anchor inserted in bone or in a vertebra in situ. Such in situ placement requires proceeding carefully so as to avoid injuries by exerting forces that are too strong. The instrument provides a hand-held device that permits easier placement of the coupling device in situ. This can be achieved gently without exerting excessive forces that may cause injuries. In particular, in spinal surgery, such a procedure may be advantageous.

Moreover, the coupling device permits, once placed onto the head of the bone anchor, a temporary locking without the requirement of a rod or a locking member. The rod can even be inserted and is not required to sit on the rod support but can be at an elevated position. Hence, by moving the locking ring from a locking position to a pre-locking position and vice versa, the bone anchoring device can be locked and unlocked to permit various adjustment steps. As such, the rod and/or the locking member are only truly needed for the final locking at the end of the surgical procedure. Therefore, the in situ placement of the coupling device with the capability of temporary and/or variable locking of the head increases the variety of correction steps that can be carried out during surgery.

With the instrument, the locking ring can be moved into the pre-locking position after placement onto the head of the bone anchor. This prevents removal of the coupling device from the head of an inserted bone anchor once the coupling device has been connected to the head of the bone anchor. Thus, the instrument can be safely detached.

According to an embodiment, the coupling device is configured to be engaged by the instrument at an inner wall of legs of the coupling device formed by the rod channel. Since an outer surface of the receiving part is not engaged by the instrument, the necessary space for placing the coupling device onto the head of a bone anchor already inserted into bone may be reduced. This permits use of narrower channels through the tissue of the human body to approach the implantation site. Hence, the instrument and the coupling device may be particularly applicable in minimally invasive surgery (MIS).

Moreover, according to an embodiment, the arms of the instrument are resiliently flexible, which gives a tactile response when attaching the instrument to the coupling device. This facilitates easier and more secure attachment of the instrument to the coupling device.

BRIEF DESCRIPTION OF THE DRAWINGS

Further features and advantages of the invention will become apparent from the description of embodiments by means of the accompanying drawings. In the drawings:

FIG. 4 shows a perspective view from a top of a receiving part of the coupling device of FIGS. 1 to 3.

FIG. 5 shows a perspective view from a bottom of the receiving part of FIG. 4.

FIG. 6 shows a top view of the receiving part of FIGS. 4 and 5.

FIG. 7 shows a cross-sectional view of the receiving part of FIGS. 4 to 6, the cross-section taken along line A-A in FIG. 6.

FIG. 8 shows a perspective view from a top of a locking ring of the coupling device of FIGS. 1 to 3.

FIG. 9 shows a perspective view from a bottom of the locking ring of FIG. 8.

FIG. 10 shows a top view of the locking ring of FIGS. 8 and 9.

FIG. 11 shows a cross-sectional view of the locking ring of FIGS. 8 to 10, the cross-section taken along line B-B in FIG. 10.

DETAILED DESCRIPTION

Figure 1:
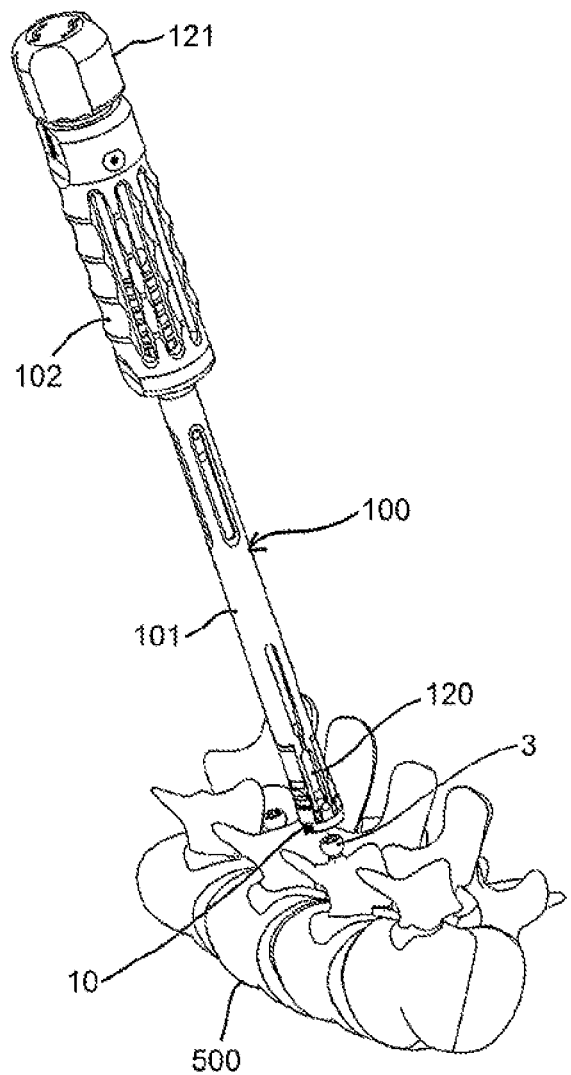
FIG. 1 shows a perspective view of a portion of a spinal column with implanted bone anchors and an instrument attached to a coupling device according to an embodiment of the invention.
Figure 2:
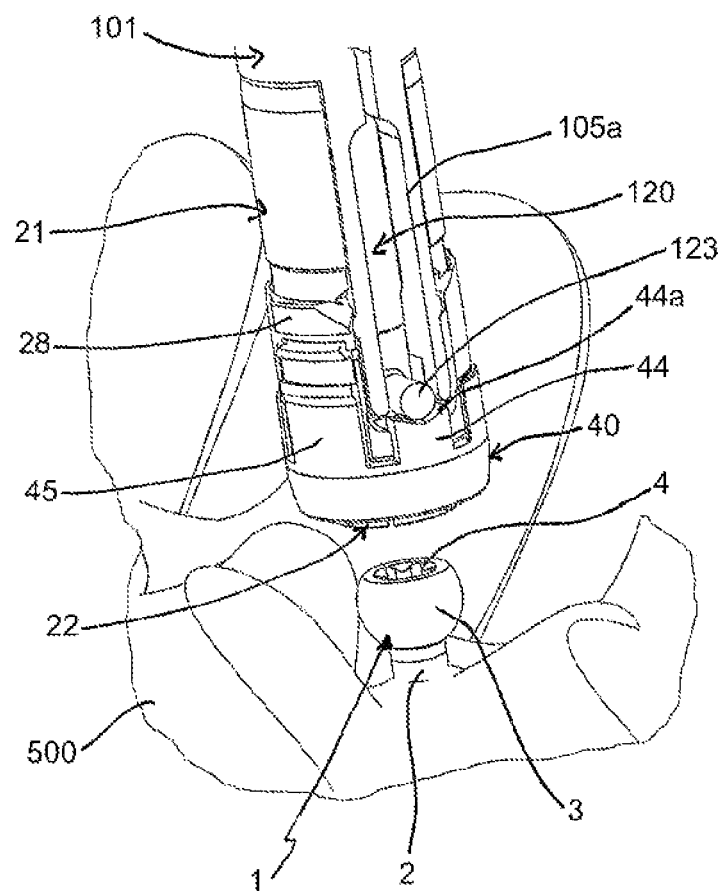
FIG. 2 shows an enlarged portion of FIG. 1.
Figure 3:
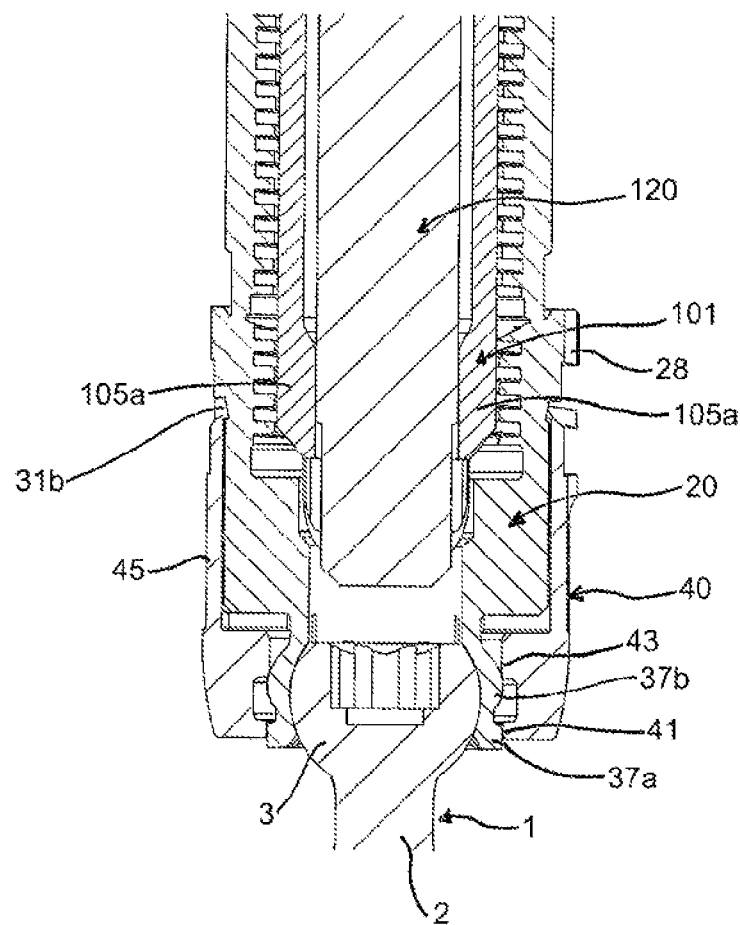
FIG. 3 shows a cross-sectional view of the embodiment of the coupling device and the instrument in FIGS. 1 and 2 placed over a head of a bone anchor, wherein the cross-section is taken in a plane including a central longitudinal axis of the instrument and that extends through centers of legs of the receiving part.
Figure 12:
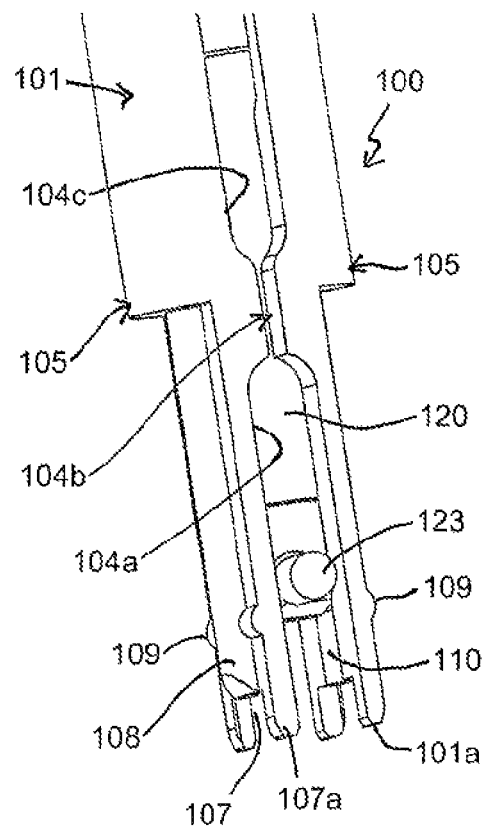
FIG. 12 shows a perspective view of a front portion of the instrument of FIGS. 1 to 3.
Figure 13:
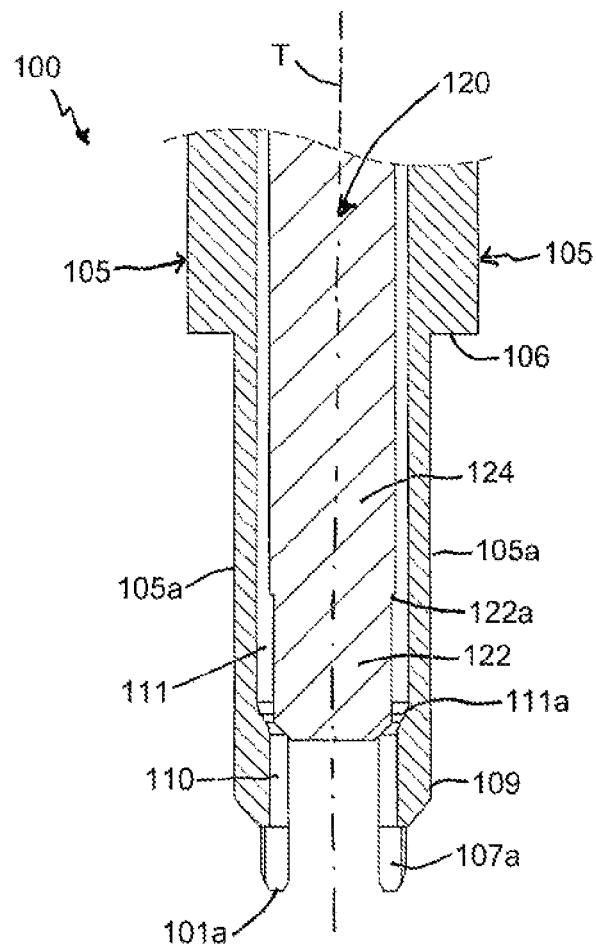
FIG. 13 shows a cross-sectional view of the front portion of the instrument of FIG. 12, the cross-section taken in a plane including a central longitudinal axis of the instrument and extending through centers of arms of the instrument.
Figure 14:
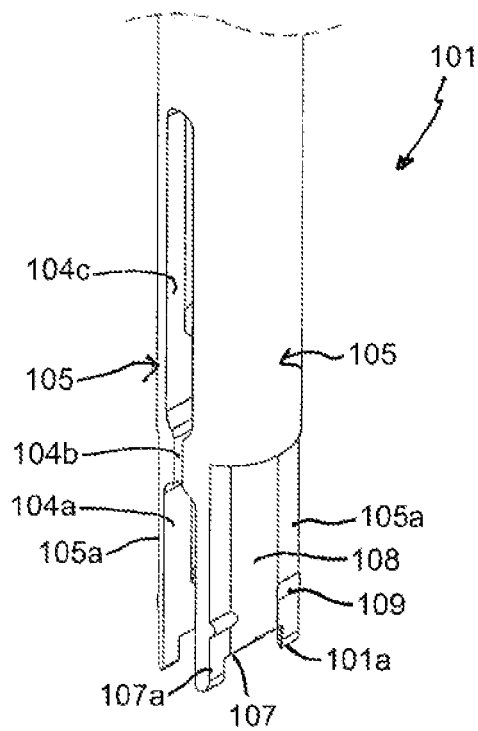
FIG. 14 shows a perspective view from a top of an end portion of a holding member of the instrument of FIGS. 12 and 13.
Figure 15:
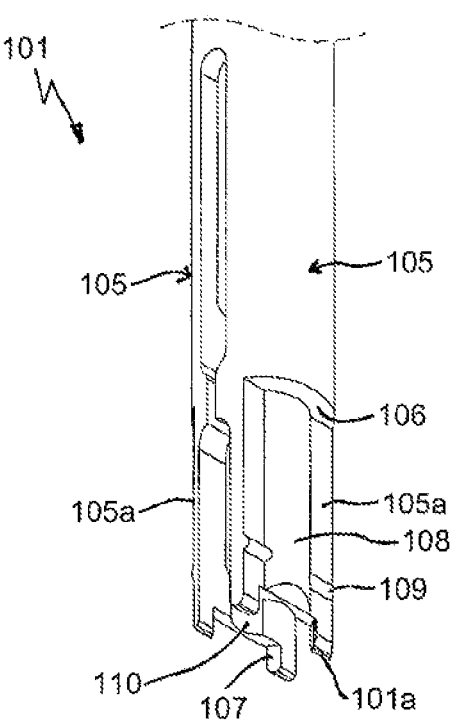
FIG. 15 shows a perspective view from a bottom of the holding member of FIG. 14.
Figure 16:
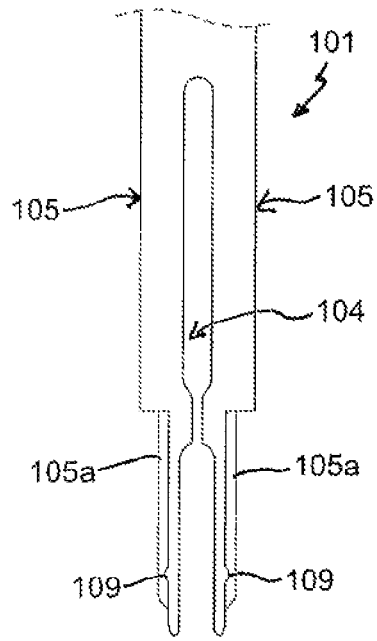
FIG. 16 shows a side view of the holding member of FIGS. 14 and 15.
Figure 17:
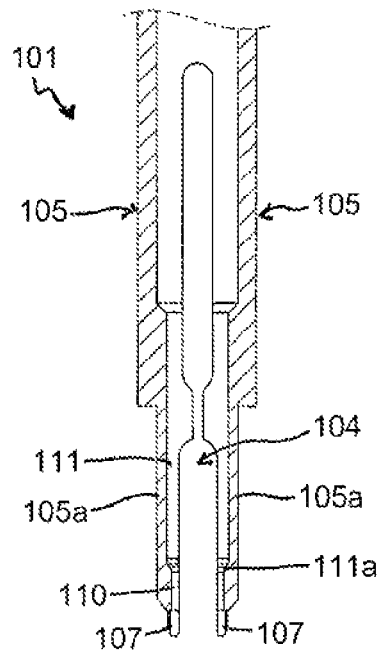
FIG. 17 shows a cross-sectional view of a front portion of the holding member of FIGS. 14 to 16, the cross-section taken in a plane including the central longitudinal axis of the instrument and extending through centers of arms of the holding member.

FIGS. 1 to 3 illustrate a first embodiment of a coupling device 10 engaged by an instrument 100 for placing the coupling device onto a head of a bone anchor. According to an embodiment, the bone anchor 1 can already be inserted into bone, for example, a pedicle of a vertebra 500, prior to mounting the coupling device thereon. The bone anchor 1 includes a shank 2 configured to be anchored in bone and a head 3. The shank 2 may have a bone anchoring structure on at least a portion thereof, such as a bone thread or barbs or any other suitable structure for anchoring. The head 3 may have a spherical outer surface portion that includes a largest outer diameter of the sphere. At a free end of the head 3, an engagement recess 4 may be provided for engagement with a screw driver. The coupling device 10 is configured to couple the bone anchor 1 to a rod (not shown), which is configured to be inserted into and fixed in the coupling device. As can be seen in particular in FIG. 3, the coupling device 10 includes a receiving part 20 and a locking ring 40. The receiving part serves for accommodating the head 3 and for receiving the rod (not shown). The locking ring 40 is configured to clamp and/or lock the head 3 in the receiving part 20. The bone anchor 1 and the coupling device 10 form a polyaxial bone anchoring device that is configured to permit coupling of the rod to the bone anchor based on various angular positions of the coupling device.

Referring additionally to FIGS. 4 to 7, the receiving part has a first or upper end 2a and a second or lower end 2b. A longitudinal central axis C extends from the upper end 2a to the lower end 2b. Adjacent to the upper end 2a, the receiving part has a rod receiving portion 21, and adjacent to the lower end 2b, the receiving part has a head receiving portion 22. The rod receiving portion 21 is substantially cylindrical, extends along the central axis C, and has a passage 23 that extends from the upper end 2a into the head receiving portion 22. The passage 23 may have regions with different diameters and/or shapes. In the embodiment, a first region 23a may be a coaxial bore with a first diameter that extends from the top end 2a to a distance from the head receiving portion 22. The first region 23a may be followed by a second region 23b which is narrower, which in turn may be followed by a third region 23c with an even more reduced diameter and which opens into the head receiving portion 22. Between the first region 23a and the second region 23b, a step 23d may be provided. Similarly, between the second region 23b and the third region 23c, a step 23e may be provided. In addition, in the second section 23b, two opposite axially extending cylinder segment-shaped recesses 39 may be formed, as best seen in FIG. 4. The recesses 39 serve as a guiding structure for a portion of the instrument 100. It shall be noted that the detailed shape of the passage may be different from the embodiment shown.

A substantially U-shaped recess 24 with a bottom 24a extends from the top end 2a to a distance from the head receiving portion 22. By means of the substantially U-shaped recess 24, two free legs 25 are formed. The recess 24 provides a channel for receiving the rod. An internal thread 26 is provided on the legs 25 and extends from substantially the upper end 2a to a distance from the bottom 24a of the recess 24. In other words, the internal thread 26 is provided along substantially the first region 23a of the passage. The internal thread 26 may be, for example, a square thread which may be advantageous for preventing splaying of the legs 25. At the lower end of the internal thread 26 that faces towards the head receiving portion 22, an undercut 26a may be formed. At a distance from the upper end 2a, a groove or otherwise weakened section 27 is provided that has a reduced wall thickness and allows breaking off of the upper portion of the legs 25. At an edge of the weakened section 27 in a circumferential direction, circumferentially extending recesses or cutouts 27a may be formed that provide further weakening of the weakened section 27 and may facilitate easier breaking off of the upper portion of the legs 25. Also, inside the passage 23, the internal thread 26 may be interrupted at an axial position that corresponds to a lower edge of the weakened section 27. Hence, the legs above the weakened portion 27 can serve as extended tabs. With the extended tabs, it is possible to manipulate the polyaxial bone anchoring device with an inserted rod that may be at a higher position with respect to the bottom 24a of the recess 24. By means of this, for example, a vertebra can be pulled against the rod.

Figure 25:
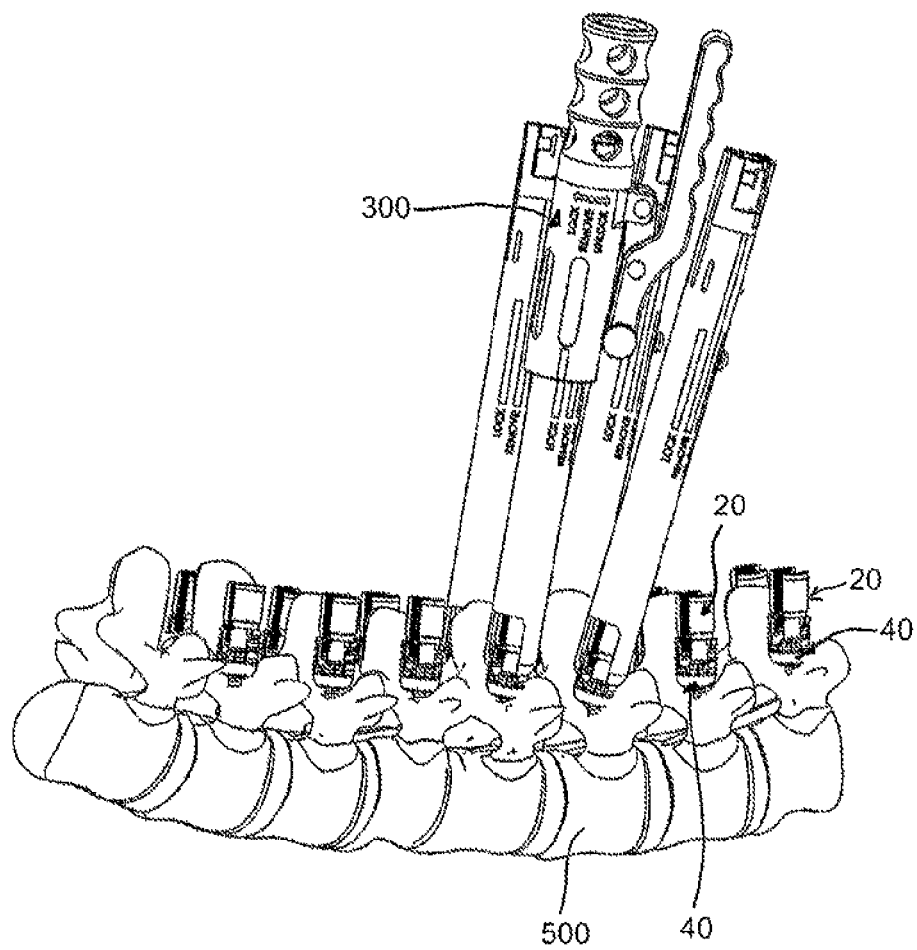
FIG. 25 shows a perspective view of a portion of a spine with inserted bone anchors and coupling devices, and attachment of another instrument for locking the coupling devices relative to the bone anchors.

At an outer surface of the rod receiving portion 21, an engagement structure for engagement with an instrument, for example, an instrument 300 as shown in FIG. 25, may be provided. The engagement structure may include circumferentially extending ribs 28, which may be arranged asymmetrical with respect to a plane including the central axis C of the receiving part 20 and a channel axis L of the substantially U-shaped recess 24. That means, a first rib can start at a distance from the edge of the U-shaped recess 24 on one side and extend to a distance around the receiving part 20. A second rib can start at the opposite side relative to the U-shaped recess and extend to a distance around the rod receiving portion. Thereby, a rib-free surface 29 is formed on each side of the U-shaped recess 24. Below each of the ribs 28, a substantially flat outer surface portion 30 may be formed that may have a contour of a rectangle or square and may serve for engagement with a portion of the locking ring 40. Between the ribs 28 and the substantially flat surface portion 30, two latching grooves or steps 31a, 31b may be provided one after the other in an axial direction. The latching grooves 31a, 31b are configured to cooperate with a portion of the locking ring 40 to provisionally hold the locking ring at one or more specific positions. The upper latching groove 31a may serve for preventing further upward movement of the locking ring in an insertion position. The lower latching groove 31b may serve for latching the locking ring in a pre-locking position.

At a position between the weakened section 27 and the bottom 24a of the substantially U-shaped recess 24, an engagement structure 32 for engagement with the instrument 100 may be provided. The engagement structure 32 may be formed as a shallow rounded groove, preferably substantially cylindrically-shaped, and may be located at the edge of the legs 25. Four such grooves may be provided, two on each leg 25 with one on either side of the leg 25. An axial position of the engagement structure 32 may be slightly below the weakened portion 27. Preferably, the shape of the engagement structure 32 is such that a corresponding engagement portion of the instrument 100 which is adapted thereto can slide into the engagement structure 32 and can slide out of the engagement structure 32. More specifically, the engagement portion of the instrument can resiliently snap into the engagement structure 32.

Furthermore, cutouts 33 may be provided on either side of the substantially U-shaped recess 24, which may serve for receiving projections of the locking ring 40 therein. By means of this, the locking ring 40 can be secured against rotation relative to the receiving part 20. From a position above the cutouts 33 to the head receiving portion 22, an external diameter or width reduction of the rod receiving portion 21 forms a step 34 that serves as a further abutment for the locking ring.

The head receiving portion 22 has a substantially cap-like shape with a hollow substantially spherical interior portion 35 forming a seat for receiving the head 3 pivotably therein. A plurality of slits 36a, 36b render the head receiving portion 22 flexible, so that, when the head 3 is inserted into the hollow interior 35, the head receiving portion 22 expands. When pressure is exerted onto an inserted head 3 by the locking ring 40, the head receiving portion 22 is compressed. The slits are open towards the lower end 2b and extend along the spherical section. Slits 36a end at the end of the spherical section, while slits 36b may extend closer to or even into a region of the rod receiving portion that defines the third region 23c of the passage 23. An outer surface of the head receiving portion 22 may be recessed in a radial direction relative to a lower end of the rod receiving portion 21. The outer surface may have a bottom section 37a that may be cylindrical or slightly outwardly tapered. The bottom section 37a forms an annular projection that is configured to cooperate with a corresponding portion of the locking ring 40. The bottom section 37a is followed by a circumferential groove and by a radially outwardly bulged portion 37b, which is configured to cooperate with another portion of the locking ring 40. The bulged portion 37b narrows in the direction towards the rod receiving portion, which contributes to the recessed shape of the head receiving portion 22.

Turning now to FIGS. 8 to 11, the locking ring 40 will be described. The locking ring 40 is designed to encompass the head receiving portion 22 and has an internal surface structure that facilitates, in cooperation with the head receiving portion 22, a full locking of an inserted head 3 in the head receiving portion 22 when the locking ring is at its lowermost position. It further facilitates a pre-locking when the locking ring is at a position slightly above the lowermost position, which still allows pivoting of the head 3 in the head receiving portion 22, but prevents removal of the head 3 from the head receiving portion 22. Lastly, the locking ring is configured to permit insertion of the head 3 into the hollow interior 35 when the locking ring is at an uppermost position relative to the receiving part.

In greater detail, the locking ring 40 has a lower surface 4b and an opposite upper surface 4a that is substantially ring-shaped. Adjacent to the lower surface 4b, there is a first radial projection 41 which projects inwardly and is configured to cooperate with the outer portion 37a at the head receiving portion. The annular projection 41 is followed by a widened section 42, which is then followed towards the upper surface 4a by a second annular projection 43 that also projects inwardly. As depicted in FIG. 3, when the locking ring 40 is mounted around the head receiving portion 22, the first annular projection 41 is configured to press onto the first portion 37a of the head receiving portion and the second annular projection 43 is configured to press onto the bulged portion 37b.

From the upper surface 4a of the ring-shaped portion of the locking ring 40, two projections 44 protrude upwardly and have a free end surface forming a rod support surface 44a for a stabilization rod. The projections 44 are diametrically opposite, i.e., offset by 180°, from one another. The rod support surface may have a substantially V-shaped cross-section to permit safe support of rods of different diameters. When the locking ring 40 is mounted to the receiving part 20 such that the upper surface 4a faces towards the upper end 2a of the receiving part, the projections 44 may extend through the cutouts 33 and thereby secure the rotational orientation of the locking ring 40 relative to the receiving part 20. The locking ring 40 also includes two upstanding arms 45 that are positioned asymmetrically with respect to a plane that extends through the central axis C and through the centers of the rod support surfaces 44a, for example, in the same or similar manner as the ribs 28 of the rod receiving portion 21 are arranged on the receiving part 20. At an upper end of the arms 45, an engagement portion in the form of circumferential ribs 46 defining a groove 46a are provided for engagement with an instrument. Such an instrument can be, for example, an instrument 300 as shown in FIG. 25. An inwardly facing upper edge 45a of the arms 45 may be provided that is configured to engage the latching grooves 31a, 31b at the receiving part 20. In the assembled state, the engagement structure in the form of the ribs 46 with the groove 46a is aligned with the engagement structure 28 at the receiving part 20, leaving the rib-free surface 29 of the receiving part 20 exposed. Moreover, the arms 45 have a substantially flat inner wall that is configured to engage the flat portion 30 at the rod receiving portion 21. Thereby, a further form-fit connection is established between the locking ring 40 and the receiving part 20. Between the projections 44 and the arms 45, there are upstanding flexible portions 47 that have a height slightly greater than that of the projections 44 and which have at an inner wall thereof a ledge 47a which is configured to abut against the step 34 on the receiving part 20.

A bone anchoring device according to an embodiment may further include a rod that is configured to be inserted into the substantially U-shaped recess 24 and a locking member, such as a set screw, that is configured to be screwed between the legs 25.

Referring to FIGS. 12 to 20, an embodiment of the instrument 100 for placing the coupling device 10 onto a head 3 of a bone anchor 1 will be described in greater detail. As shown additionally in FIG. 1, the instrument 100 includes a substantially tubular holding member 101 and a shaft-like pushing member 120 that is arranged inside the holding member 101. The holding member 101 has a rear portion that is connected to or provided with a handle 102 and an opposite front portion. The front portion is bifurcated through a slot 104 that forms two arms 105 which are configured to be flexibly compressible and expandable in a transverse direction relative to a longitudinal tube axis T of the holding portion. The slot 104 extends from a free end portion 101a of the holding member 101 in a substantially U-shaped manner with a bottom facing towards a rear end of the holding member. From the bottom of the slot a substantially straight portion 104b continues and opens into an elongate portion 104c. It shall be noted that the slot may have different shapes for obtaining various different degrees of flexibility.

The arms 105 have a front portion 105a adjacent to the free end portion 101a. The front portion 105a is recessed from an overall cylindrical shape of the holding member so as to fit into the rod receiving portion of the receiving part 20. Through the recessed arrangement of the front portion 105a of the arms 105, an abutment face 106 is provided at the end of the front portion 105a which may abut against the upper end 2a of the receiving part when the front portion 105a of the arms is inserted into the rod receiving portion. The front portions 105a of the arms each has a recess 107 adjacent to the free end 101a, which may be substantially rectangular. By the recess 107, two short legs 107a are formed on each of the front portions 105a of the arms 105. This design permits the front portions 105a of the arms to extend downward into a lowermost region of the substantially U-shaped recess 24. An outer surface of the front portion 105a includes an axially extending substantially cylinder segment-shaped rib or projection 108 which is configured to engage the cylindrical recess 39 in the second section 23b of the rod receiving portion 21.

Furthermore, at a distance from the abutment face 106, each arm 105 includes an engagement portion 109 which is configured to engage the engagement structure 32 at the rod receiving portion 21. In greater detail, the engagement portion 109 may be formed as a cylindrical projection with a cylinder axis transverse to the longitudinal axis T of the holding portion and arranged and configured to engage the groove 32. As can be seen in particular in FIGS. 12 and 14 to 15, each front portion 105 includes two engagement portions 109 which are located to the left and to the right of the axial cylindrical projection 108. The arms 105 may be substantially flat at their outer surface except in the region of the axial projection 108 and the engagement portions 109. At an inner wall of the front portions 105a, coaxially extending cylindrical recesses 110 are formed in a region adjacent to the recesses 107 and provide guidance for the pushing member 120. Adjacent to the recesses 110, the front portions 105a of the arms may include, at their inner side, a widened diameter section 111 to provide sufficient space for permitting the pushing member 120 to slide therethrough. A stepped portion 111a is formed between the recess 110 and the widened diameter section 111, which may form an abutment for a stepped portion at an outer surface of the pushing member, as explained further below.

Figure 18:
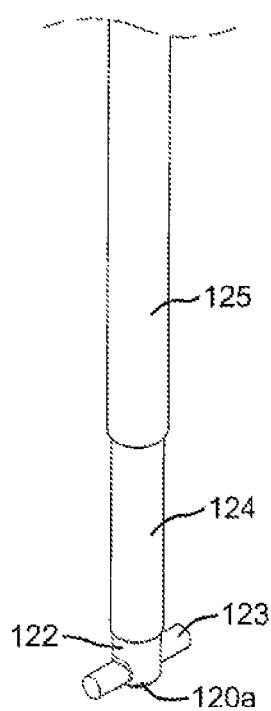
FIG. 18 shows a perspective view from a top of a front portion of a pushing member of the instrument of FIGS. 12 to 13.
Figure 19:
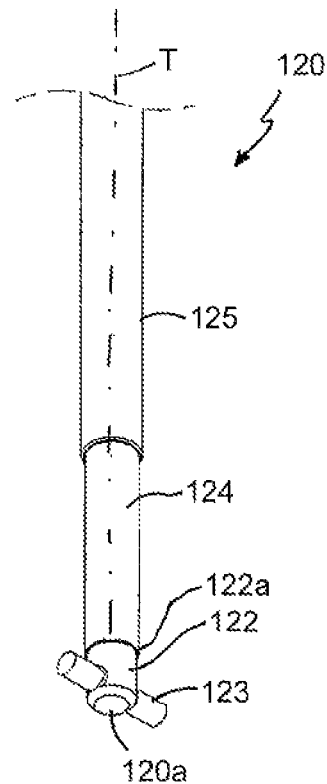
FIG. 19 shows a perspective view from a bottom of the pushing member of FIG. 18.
Figure 20:
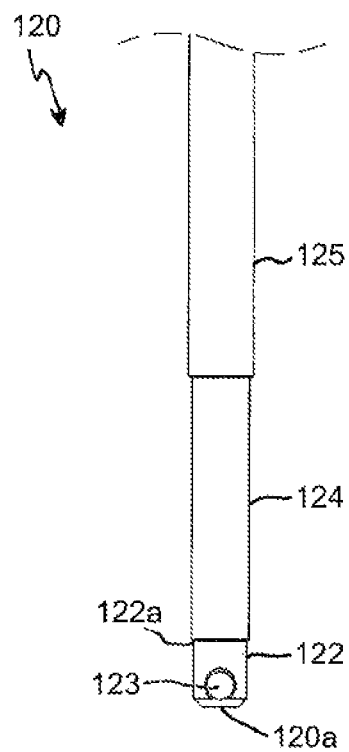
FIG. 20 shows a side view of the front portion of the pushing member of FIGS. 18 and 19.

Turning now in particular to FIGS. 18 to 20, the pushing member 120 will be described. As generally shown in FIG. 1, the pushing member 120 may be connected at a rear side thereof to a knob 121 which is adapted to displace the pushing member 120 relative to the holding member 101. In the handle 102, there may be additionally housed a mechanism (not shown) that translates a rotating movement of the knob 121 into an axial displacement of the pushing member 120 relative to the holding member 101. Various mechanisms may be contemplated to displace the pushing member 120 relative to the holding member. For example, a mechanism may be designed such that by rotating the knob 121, the pushing member can be pushed axially to a maximum position relative to the holding member, and where further rotating the knob 121 will retract the pushing member from the maximum axial position.

The front portion of the pushing member 120 is shown in detail in FIGS. 18 to 20. Adjacent to a free end 120a, the pushing member 120 includes a first substantially cylindrical section 122 with an outer diameter that is configured to fit into the axial cylindrical recesses 110 at the inner wall of the front portions 105a of the holding member (see also FIG. 13). Adjacent or close to the free end 120a, an elongate engagement portion 123 is provided that extends transverse to the longitudinal axis T, in particular, that extends perpendicular to the longitudinal axis. The elongate engagement portion 123 has in the embodiment shown a rod-shape, and may be realized, for example, by a pin extending through a transverse hole in the front portion 122. A length of the elongate engagement portion 123 is at least greater than the distance between the projections 44 on the locking ring 40, such that the rod support surface 44a of the projections 44 can be engaged by the elongate engagement portion 123. In other words, the elongate engagement portion 123 forms a kind of dummy rod that is configured to push onto the rod support surface 44a. Adjacent to the first cylindrical section 122, a second section 124 which has a slightly greater outer diameter may be provided so that a shoulder 122a is formed between the second section 124 and the first section 122. The shoulder is configured to abut against the stepped portion 111a in the inner side of the holding member 101. The length of the second section may be such that it extends further proximally into the holding member than a length of the front portions 105a of the arms. Furthermore, for more stability, a third section 125 with a still greater diameter may be provided.

The front portion 105a of the arms is configured to be inserted into the rod receiving portion 21 and is sized such that when the abutment face 106 abuts against the upper end 2a of the receiving part 20, the legs 107a extend to a short distance from the bottom 24a of the substantially U-shaped recess 24 of the receiving part 20. In this position, the engagement portion 109 is at an axial height that permits engagement with the engagement structure 32 at the receiving part.

The parts and portions of the bone anchor, the coupling device, and the instrument may be made of any material, preferably, however, of a bio-compatible material, such as titanium or stainless steel, or any other bio-compatible metal or metal alloy, or a plastic material. As a bio-compatible alloy, a NiTi alloy, for example, Nitinol, may be used. Other materials that can be used are magnesium or magnesium alloys. Bio-compatible plastic materials that can also be used may be, for example, polyether ether ketone (PEEK) or poly-L-lactide acid (PLLA). The parts can be made of the same or of different materials from one another.

Figure 21D:
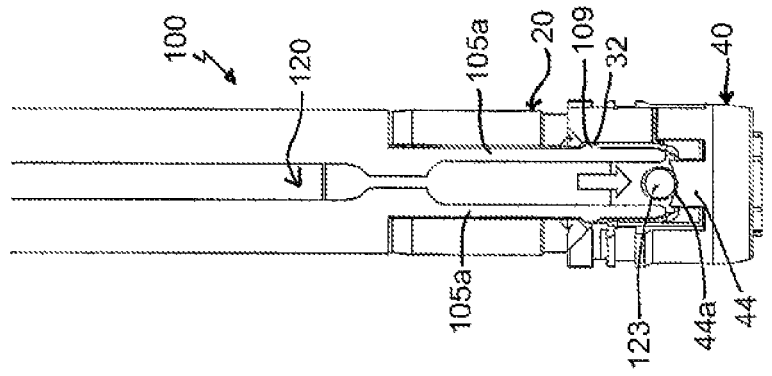
FIGS. 21a to 21d show side views of steps of attaching the instrument to the coupling device according to an embodiment of the invention.
Figure 21C:
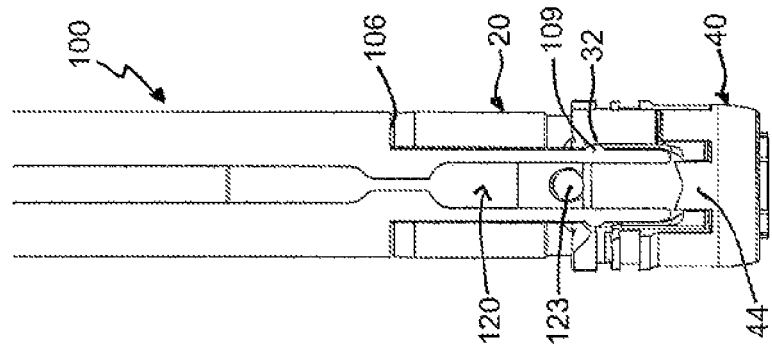

Use of the coupling device 10 and the instrument 100 will be described with reference to FIGS. 21a to 24c. First, steps of assembling the coupling device 10 and the instrument 100 will be described. The coupling device may include the receiving part 20 and the locking ring 40 in a pre-assembled manner. As shown in FIG. 21a, the pushing member 120 is in a retracted position farther away from the free end portion 101a of the holding member than the engagement portions 109. The locking ring 40 is mounted onto the receiving part such that the projections 44 engage the cutouts 33 of the receiving part. For engagement with the instrument 100, the locking ring 40 may be at the insertion position in which the edge 45a of the arms 45 abuts against the axially higher located latching step 31a. In the insertion position, the head 3 can enter into the hollow interior 35 of the head receiving portion 22. The distance between the front portions 105a of the arms 105 is such that when the front portions of the arms are introduced between the legs 25 of the coupling device, the front portions 105a are compressed towards each other.

Figure 21B:
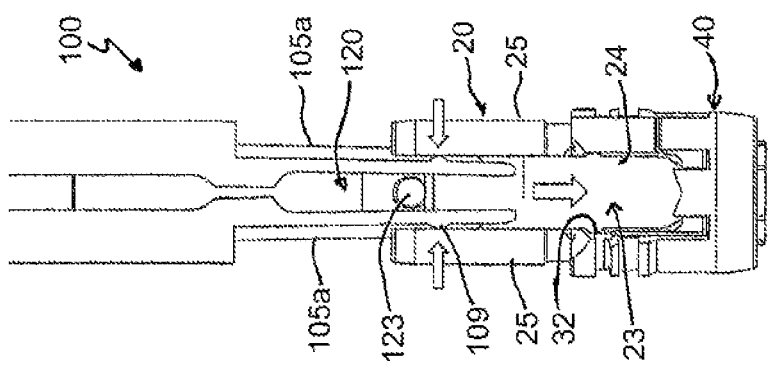
Figure 21A:
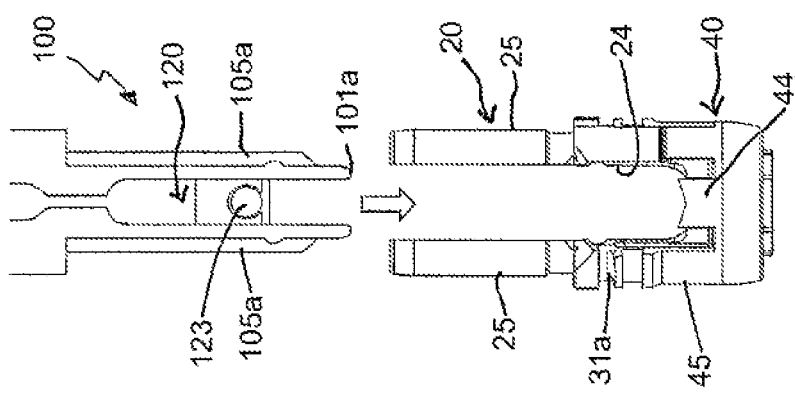

As shown in FIG. 21b, when the front portions 105a of the arms are compressed towards each other by the inner wall of the legs 25, the front portions 105a can advance deeper into the passage 23. When the engagement portions 109 at the outer wall of the front portions 105a of the arms reach the engagement structure 32 at the receiving part 20, the engagement portions 109 snap into the engagement structure 32 as depicted in FIG. 21c. The holding member 101 can then be fixedly connected to the receiving part 20, since the front portions 105a of the arms 105 can be prevented from being compressed inwards. As a result, the coupling device 10 can be fixedly connected to the instrument. FIG. 21d shows the fixed connection between the holding member 101 and the receiving part 20, with the pushing member 120 at a pushed-forward position in which the elongate engagement portion 123 contacts the rod support surface 44a.

Figure 22:
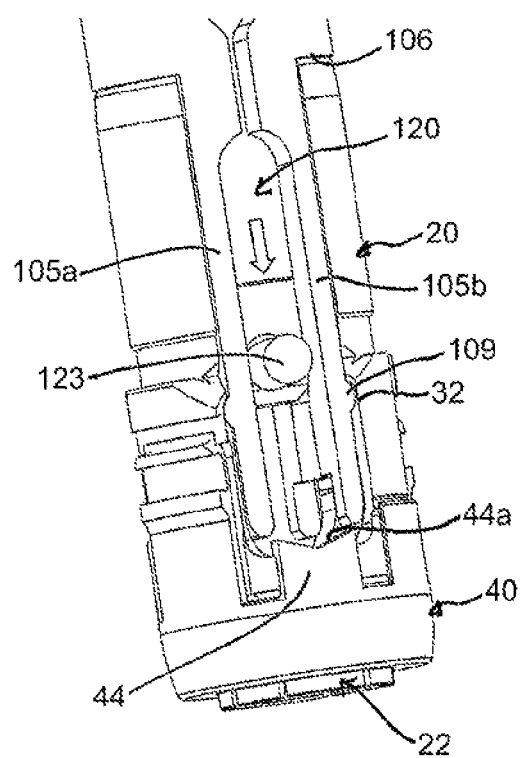
FIG. 22 shows a perspective view of a step of fixing the front portion of the instrument to the coupling device.
Figure 23:
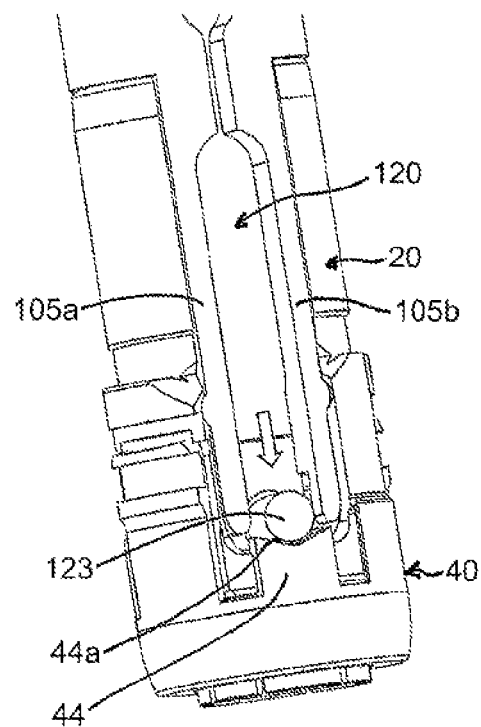
FIG. 23 shows a perspective view of a step of adjusting a pre-locking position of the locking ring relative to the receiving part with the instrument.

FIGS. 22 and 23 show in a more detailed perspective view the positions of the pushing member 120 relative to the holding member 101. In FIG. 22, the pushing member is at a position above the engagement portions 109 and the engagement structure 32, and begins to spread the front portions 105a of the arms as it moves down. In FIG. 23, the pushing member has been pushed downward until the elongate engagement portion 123 is slightly above the rod support surface 44a of the projections 44. The elongate engagement portion 123 may not yet contact the rod support surface 44a. From this position, only a small axial movement of the pushing member farther downwards is necessary for the elongate engagement portion 123 to push onto the rod support surface 44a. This in turn moves the locking ring 40 downward, so that the annular projection 41 of the locking ring can engage the bottom portion 37a at the outer surface of the head receiving portion 22. Thereby, the lower opening of the hollow interior 35 can be narrowed in such a manner that an inserted head 3 cannot be removed.

Figure 24C:
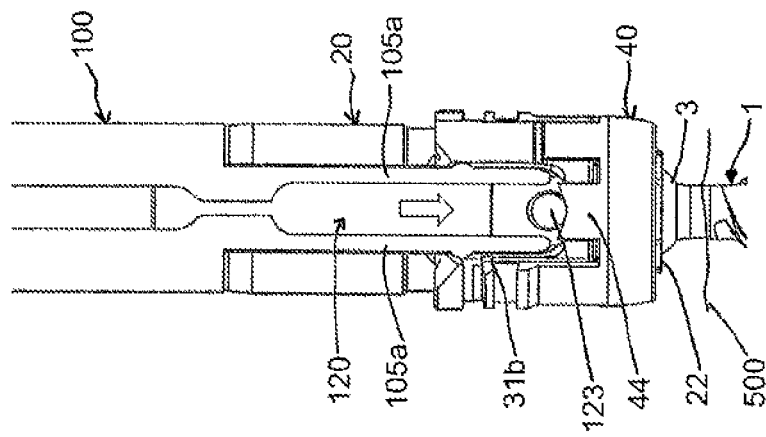
FIGS. 24a to 24c show steps of using the instrument to place the coupling device onto a head of a bone anchor inserted into bone.
Figure 24B:
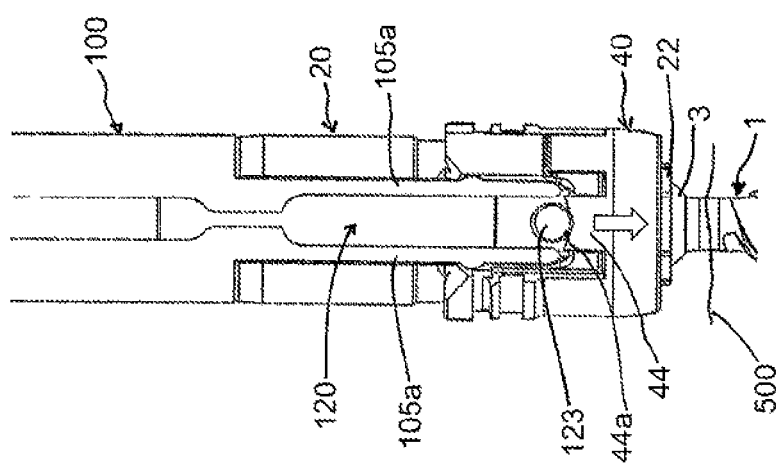
Figure 24A:
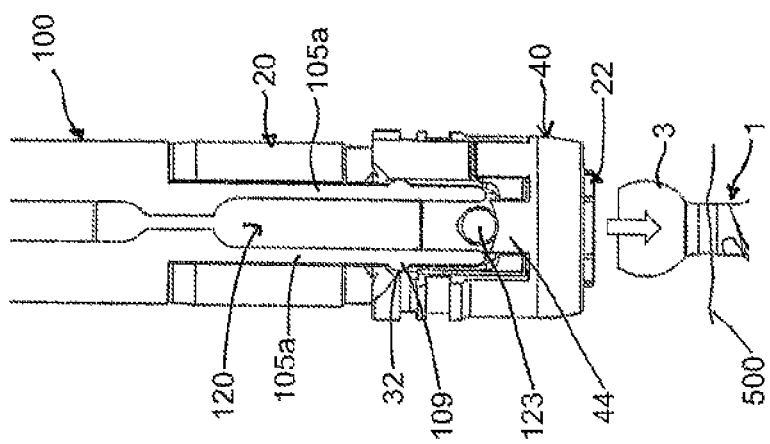

Referring to FIGS. 24a to 24c, the placement and use of the coupling device 10 and the instrument 100 together with a bone anchor 1 are shown. In FIG. 24a the shank 2 has been inserted into a bone, for example into a vertebra 500 prior to mounting the coupling device onto the head. The instrument is fixedly connected to the coupling device and the locking ring is at the insertion position wherein the head receiving portion can expand to let the head 3 enter. The engagement portion 123 does not yet press onto the rod support surface 44a. As depicted in FIG. 24b, the coupling device is placed by means of the instrument 100 onto the head 3. In doing this, the head 3 snaps into the hollow interior 35 of the head receiving portion 22 and may be held there by friction. In a next step shown in FIG. 24c, the pushing member 120 is moved towards or downward against the locking ring 40. Further downward movement of the pushing member pushes the locking ring 40 downward until the engagement portion 123 contacts the rod support surface 44a of the projections 44, as shown in FIG. 24c. Thereby, the arms 45 snap with their edge 45a into the lower latching recess 31b at the receiving part. The locking ring 40 is now latched at the pre-locking position. In addition, the ledge 47b of the projection 47 may snap under the step 34 at the outer surface of the rod receiving portion which further secures the pre-locking position. After achieving the pre-locking position, the pushing member 120 is retracted. When the pushing member 120 is moved to a higher position in which it no longer blocks inward movement of the engagement portions 109 and detachment from the engagement structure 32, the flexible front portions 105a of the arms can be compressed towards each other and the instrument can be removed from the coupling device.

After placement of the coupling device, the polyaxial bone anchoring device is in the pre-locking position. The head may be held by friction in the seat so that the coupling device can assume an angular position relative to the shank which can be maintained provisionally prior to final locking.

In clinical use, a plurality of polyaxial bone anchoring devices are inserted into bone parts or into vertebrae, as shown in FIG. 25, for example, into the pedicles of vertebrae 500. The coupling devices 10 are then aligned so that a rod (not shown) can be received in the rod receiving portions of two or more of the bone anchoring devices. With, for example, another instrument 300 different from the instrument 100 described above, as shown schematically in FIG. 25, it may further be possible to move the locking ring from the pre-locking position to a locking position and also to release the locking position. In the locking position, the locking ring 40 is moved further downward until the head receiving portion 22 is firmly compressed so that the head is locked therein. The instrument 300 may include, for example, an outer tube for engaging the locking ring, for example at the engagement portions 28, and an inner tube for engaging the rod receiving portion. The inner tube may be displaceable relative to the outer tube, so that by displacing the outer tube relative to the inner tube, the locking ring can be moved from the pre-locking position to the locking position and vice versa. The adjustments of the coupling device relative to the bone anchor can be performed without a rod and/or a locking member placed into the rod receiving portion, or the rod can be at an elevated position relative to the bottom 24a of the recess 24. It shall be noted that locking and unlocking can be carried out several times. When the coupling device has been adjusted to a correct or desired position, the coupling device can be locked to the bone anchor using a locking member screwed between the legs 25. Finally, the upper portion of the legs may be broken-off.

Modifications of the embodiments described may further be contemplated. The parts are not limited to their detailed shape as depicted in the embodiments. In particular, the specific shape of the receiving part and of the locking ring may vary. The shape and structure of the engagement between the receiving part and the instrument can also be different from the embodiments shown. The design of the instrument for placing the coupling device onto the head, in particular the front portion, is not limited to the specific designs shown in the embodiments. Other shapes may also be suitable. For example, the instrument may also engage the receiving part at an outer surface thereof.

The rod can be any elongate device that is configured to connect two bone anchoring devices. For the bone anchor, all kinds of bone anchors, such as bone screws, bone nails, etc., may be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling device for coupling a rod to a bone anchor, the coupling device comprising:
    a receiving part comprising:
        a head receiving portion defining a seat for pivotably receiving a head of the bone anchor, the head receiving portion being expandable to permit insertion of the head and compressible to lock the head in the seat; and
        a rod receiving portion defining a recess for receiving the rod, the recess having a bottom and forming two legs, wherein the rod receiving portion comprises an engagement structure for engaging a locking member to lock the rod in the recess, and a first engagement surface different from the engagement structure for engaging an instrument, wherein the first engagement surface is formed on a region other than radially outwardly facing regions of the rod receiving portion; and
    a locking ring positionable around the head receiving portion, the locking ring comprising a second engagement surface for engaging the instrument;
    wherein when the locking ring is around the head receiving portion, the locking ring can assume an insertion position where the head of the bone anchor is insertable into the head receiving portion, and a pre-locking position where the head is prevented from removal from the head receiving portion.

2. The coupling device of claim 1, wherein the first engagement surface comprises a recess or a projection engageable with a corresponding projection or recess at the instrument.

3. The coupling device of claim 2, wherein the recess or projection is formed on each of the legs.

4. The coupling device of claim 1, wherein the first engagement surface is formed on a region of the rod receiving portion that defines the recess for the rod.

5. The coupling device of claim 1, wherein the second engagement surface forms a rod support for an inserted rod.

6. The coupling device of claim 5, wherein the rod support comprises two projections that are offset by 180° from one another.

7. The coupling device of claim 1, wherein the receiving part comprises a third engagement surface engageable with the locking ring to restrict movement of the locking ring from the insertion position in a direction away from the pre-locking position.

8. The coupling device of claim 1, wherein the receiving part comprises a third engagement surface engageable with the locking ring to restrict movement of the locking ring from the pre-locking position towards the insertion position.

9. The coupling device of claim 1, wherein the locking ring can further assume a locking position relative to the head receiving portion where the head is locked relative to the receiving part.

10. An instrument for placing a coupling device onto a head of a bone anchor, the coupling device comprising a receiving part comprising a head receiving portion for pivotably receiving the head of the bone anchor and a rod receiving portion for receiving a rod, and a locking ring movable around the head receiving portion from an insertion position where the head of the bone anchor is insertable into the head receiving portion to a pre-locking position where the head is prevented from removal from the head receiving portion, the instrument having a longitudinal axis and comprising:
    a holding member having a front portion engageable with the receiving part, the front portion having a first width measured in a direction transverse to the longitudinal axis; and
    a pushing member that extends through and is movable axially relative to the holding member, wherein the pushing member comprises a projection having a width measured in the direction transverse to the longitudinal axis that is greater than the first width to engage the locking ring.

11. The instrument of claim 10, wherein the front portion of the holding member comprises two arms insertable between legs of the receiving part to engage the rod receiving portion.

12. The instrument of claim 11, wherein the arms are movable away from one another and comprise engagement portions for engaging the legs.

13. The instrument of claim 12, wherein the pushing member is movable between the arms to radially expand the arms for fixing the holding member to the receiving part.

14. The instrument of claim 10, wherein the projection of the pushing member is elongate and has a longitudinal axis that extends substantially transversely to the longitudinal axis of the holding member.

15. A system comprising the instrument of claim 10 and the coupling device comprising the receiving part and the locking ring.

16. A method of connecting a coupling device to a bone anchor for the purpose of coupling a rod to a bone, the coupling device comprising a receiving part comprising a head receiving portion defining a seat for pivotably receiving a head of the bone anchor, the head receiving portion being expandable to permit insertion of the head and compressible to lock the head in the seat, a rod receiving portion defining a recess for receiving the rod, the recess having a bottom and forming two legs, wherein the rod receiving portion comprises an engagement structure for engaging a locking member to lock the rod in the recess, and a first engagement surface different from the engagement structure for engaging an instrument, and a locking ring positionable around the head receiving portion, the locking ring comprising a second engagement surface for engaging the instrument, wherein a plane defined by a longitudinal axis of the coupling device and a longitudinal axis of the recess for the rod separates the coupling device into a first side and a second side, and wherein on the first side of the coupling device, the first and second engagement surfaces each has at least a portion located at a distinct circumferential position relative to the longitudinal axis of the coupling device from which the entire other one of the first and second engagement surfaces is spaced apart circumferentially, the method comprising:

anchoring the bone anchor to bone;

inserting the head of the bone anchor into the head receiving portion of the coupling device when the locking ring is around the head receiving portion at an insertion position;

adjusting the locking ring from the insertion position to a pre-locking position where the head is prevented from removal from the head receiving portion; and adjusting an angular position of the coupling device relative to the bone anchor.

17. The method of claim 16, wherein the bone anchor is anchored to bone prior to inserting the head of the bone anchor into the head receiving portion of the coupling device.

18. The method of claim 16, further comprising connecting an instrument to the first engagement surface of the receiving part to facilitate the insertion of the head of the bone anchor into the head receiving portion of the coupling device.

19. The method of claim 18, wherein the instrument is further configured to engage the second engagement surface to adjust the position of the locking ring.

20. The method of claim 18, further comprising using the instrument to adjust the locking ring from the insertion position to the pre-locking position to prevent removal of the head from the head receiving portion.

21. The method of claim 16, further comprising inserting a rod into the recess after the adjusting of the angular position of the coupling device relative to the bone anchor, and advancing the locking member into the recess to lock the rod and the bone anchor relative to the coupling device.

22. The method of claim 16, wherein the first engagement surface is formed on a region other than radially outwardly facing regions of the rod receiving portion.

\* \* \* \* \*